United States Patent
Kubein-Meesenburg et al.

(10) Patent No.: US 6,780,013 B2
(45) Date of Patent: Aug. 24, 2004

(54) DENTAL ABRADING BODY FOR TREATING TOOTH CROWDING

(76) Inventors: Dietmar Kubein-Meesenburg, Robert-Koch-Strasse 40, Goettingen (DE), D-37075; Dankmar Ihlow, Roegen 41, Sierksdorf (DE), D-23730; Hans Naegerl, Lange Hecke 41, Gleichen (DE), D-37130

(*) Notice: Subject to any disclaimer, the term of this patent is extended or adjusted under 35 U.S.C. 154(b) by 19 days.

(21) Appl. No.: 10/096,058

(22) Filed: Mar. 13, 2002

(65) Prior Publication Data

US 2002/0137009 A1 Sep. 26, 2002

Related U.S. Application Data

(63) Continuation of application No. PCT/DE00/02469, filed on Jul. 26, 2000.

(30) Foreign Application Priority Data

Sep. 13, 1999 (DE) .......................... 199 43 868

(51) Int. Cl.[7] .............................. A61C 3/06; A61C 5/00
(52) U.S. Cl. ....................................... 433/166; 433/215
(58) Field of Search ................................ 433/142, 166, 433/215

(56) References Cited

U.S. PATENT DOCUMENTS

| | | | | |
|---|---|---|---|---|
| 2,411,234 A | * | 11/1946 | Silver | .......................... 433/122 |
| 4,353,696 A | * | 10/1982 | Bridges | ........................ 433/125 |
| 4,731,019 A | * | 3/1988 | Martin | ......................... 433/119 |
| 5,476,381 A | | 12/1995 | Dragan | ......................... 433/142 |
| 6,022,217 A | * | 2/2000 | Hugo | .......................... 433/166 |
| 6,267,594 B1 | * | 7/2001 | Hugo | .......................... 433/119 |

FOREIGN PATENT DOCUMENTS

| | | |
|---|---|---|
| CH | 652587 | 11/1985 |
| DE | 652270 | 10/1937 |
| DE | 897473 | 7/1949 |

* cited by examiner

*Primary Examiner*—John J. Wilson
(74) *Attorney, Agent, or Firm*—Crowell & Moring LLP

(57) ABSTRACT

An abrading body (1) for treating tooth crowding, which can be introduced into interdental spaces (10) between teeth (9) and is provided with oppositely disposed working or abrading surfaces (2, 3) on both sides thereof and a shaft for attachment to a reciprocating drive mechanism (8). The abrading body (1) can be introduced vertically between the teeth (9), i.e., in the longitudinal direction thereof, and is designed to carry out an abrading movement in this direction. The abrading surface (3) is formed with a convex cross-sectional configuration. The opposite abrading surface (2) is formed with a concave cross-sectional configuration. The radius (R3) of the convex abrading surface (3) is greater than the radius (R2) of the concave abrading surface (2). An advantageous interdental contact in the form of an overlapping, dimeric, arcuate chain of teeth can be created by introducing concave and convex contact surfaces on adjacent teeth using the tooth abrading body (1) of the invention.

3 Claims, 2 Drawing Sheets

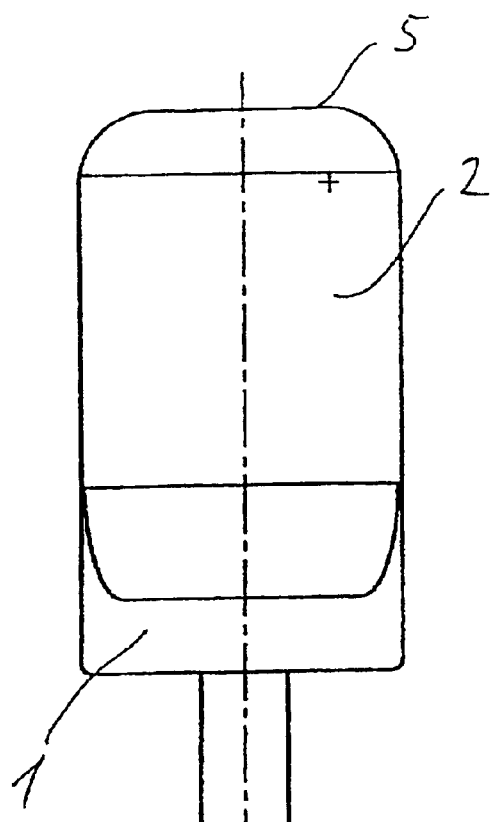
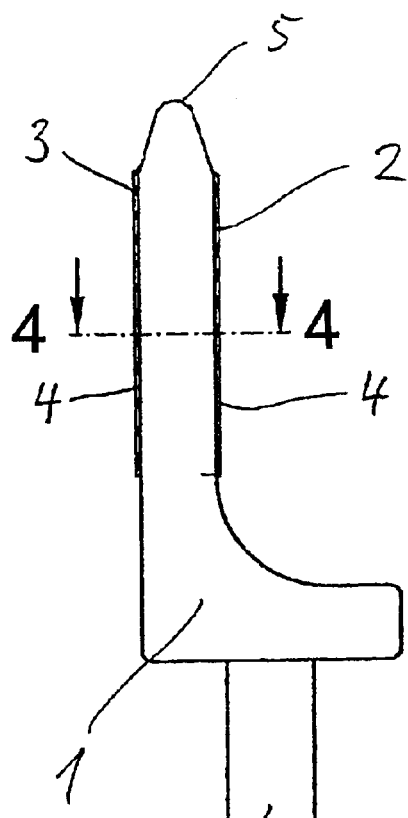
Fig. 1
Fig. 2
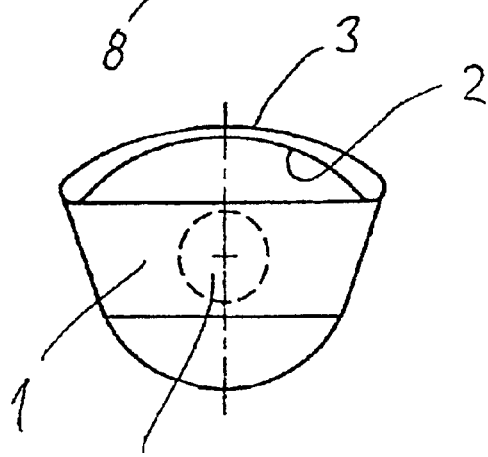
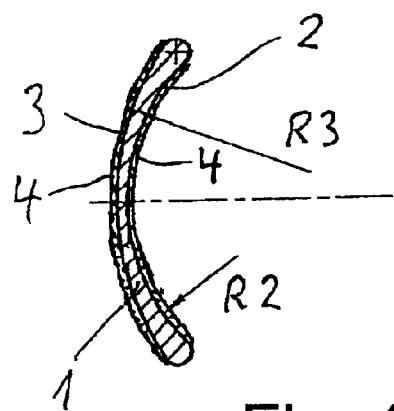
Fig. 3
Fig. 4

DENTAL ABRADING BODY FOR TREATING TOOTH CROWDING

CROSS REFERENCE TO RELATED APPLICATIONS

This application is a continuation of international patent application no. PCT/DE00/02469, filed Jul. 26, 2000, designating the United States of America, the entire disclosure of which is incorporated herein by reference. Priority is claimed based on Federal Republic of Germany patent application no. DE 199 43 868.4, filed Sep. 13, 1999.

BACKGROUND OF THE INVENTION

The invention relates to a dental abrading body for treating tooth crowding. This abrading body can be introduced into the interdental spaces between the teeth. It is provided with opposite abrading or working surfaces on both sides thereof and with a connecting member for attachment to a reciprocating drive mechanism.

One treatment method for tooth crowding is to eliminate tooth rotations by means of a fixed or a removable apparatus. In this case, however, the recurrence rate is relatively high.

It is also known in the art to use a dental abrading body, which is introduced horizontally into the interdental spaces, i.e. perpendicularly to the longitudinal direction of the teeth, in order to remove tooth substance in the interdental contact area through a horizontal abrasion movement. This creates space between the teeth. Drawbacks of using these prior art dental abrading bodies include the fact that the horizontal abrasion movement is uncomfortable or painful for the patient, and the fact that that this method only allows flat abrasion surfaces to be created.

SUMMARY OF THE INVENTION

An object of the invention is to provide an improved dental abrading body for treating tooth crowding.

Another object is to provide a dental abrading body which can be used prophylactically to produce contact and position stability of the teeth.

A further object of the invention is to provide a dental abrading body which can produce an anti-rotational interlock between adjacent teeth.

These and other objects have been achieved in accordance with the present invention by providing a dental abrading body which can be introduced into interdental spaces for treating tooth crowding, the abrading body being provided with first and second working surfaces on opposite sides thereof and having a connector for attachment to a reciprocating drive mechanism, and in which dental abrading body can be introduced vertically between the teeth and is designed for vertical abrasion movements; one working surface of the abrading body has a convex cross-sectional shape having a radius of curvature R3, and the other working surface has a concave cross-sectional shape having a radius of curvature R2; and the radius of curvature of the convex working surface is greater than the radius of curvature of the concave working surface.

The dental abrading body according to the invention can be introduced vertically between the teeth, i.e. in their longitudinal direction, and it is designed for use with vertical abrasion movements. One of the abrading or working surfaces has a convex cross-sectional shape, and the opposite abrading or working surface has a concave cross-sectional shape. The radius of the convexly curved working surface is greater than the radius of the concavely curved working surface.

In a natural set of teeth, the teeth contact one another with convex surfaces. Thus, for natural teeth, the interdental contact can be represented by a dimeric link chain. The drawback is that such a straight dimeric link chain is unstable, which causes the teeth to rotate in relation to one another if the available space in the dental arch is not sufficient.

The inventive dental abrading body makes it possible to produce a favorable interdental contact in the form of an overlapping dimeric arcuate chain of teeth. The convex working surface of the dental abrading body forms a concave contact surface in the contact area of the one tooth. At the same time, as a rule, the concave working surface of the dental abrading body adapts the radius of the existing convex contact surface of the adjacent contact tooth to the concave contact surface. Preferably, the concave contact surface is formed with a larger radius of curvature than the convex contact surface.

However, with a non-abrasive embodiment of the concave working surface of the dental abrading body, it is also possible to use the convex tooth surface only as a guide surface for the abrading body, so that the convex contact surface of the tooth, if it fits, is maintained in its natural state.

The overlapping dimeric arcuate chain of teeth, which is created by shaping the concave and convex contact surfaces in the interdental area, is distinguished by excellent pressure stability due to the interlocking or form-fit engagement of the contact surfaces. As a result, the contact and position stability of the adjacent teeth is enhanced. After correction of misaligned tooth positions, this stability guards against recurrence and prevents or reduces tertiary crowding.

A further advantage of treatment with the inventive dental abrading body is that only a minimum amount of the approximal enamel has to be removed along the contact surfaces of the teeth to obtain physical stability for each contact, i.e., for instance, in the anterior dental arch. The space obtained as a result is 0.25 to 0.35 mm per contact surface. The artificial concave-convex abrasions, which are being created alter the contacts to form a stable overlapping dimeric chain of teeth. In addition, a vertical abrasion movement is less painful for a patient than a horizontal abrasion movement.

Preferably, both abrading or working surfaces of the dental abrading body are coated with diamond abrasive to permit simultaneous precise shaping of the corresponding concave and convex contact surfaces on the teeth in the interdental area. Alternatively, if the natural convex curvature of the contact surface of a tooth can be retained without treatment, only the convex working surface of the dental abrading body for shaping the concave contact surface is diamond-coated.

In accordance with a preferred embodiment, the front edge of the dental abrading body is not diamond-coated to make it easier to introduce it between the teeth. For the same reason, it may be advantageous to taper the front edge of the dental abrading body.

BRIEF DESCRIPTION OF THE DRAWINGS

The invention will be described in further detail hereinafter with reference to illustrative preferred embodiments shown in the accompanying drawings in which:

FIG. 1 is a front elevational view of a first dental abrading body according to the invention;

FIG. 2 is a side elevational view of the dental abrading body of FIG. 1;

FIG. 3 is a top plan view of the dental abrading body of FIG. 1;

FIG. 4 is a cross section along line 4—4 through the dental abrading body of FIG. 1;

DETAILED DESCRIPTION OF PREFERRED EMBODIMENTS

Figure 5:
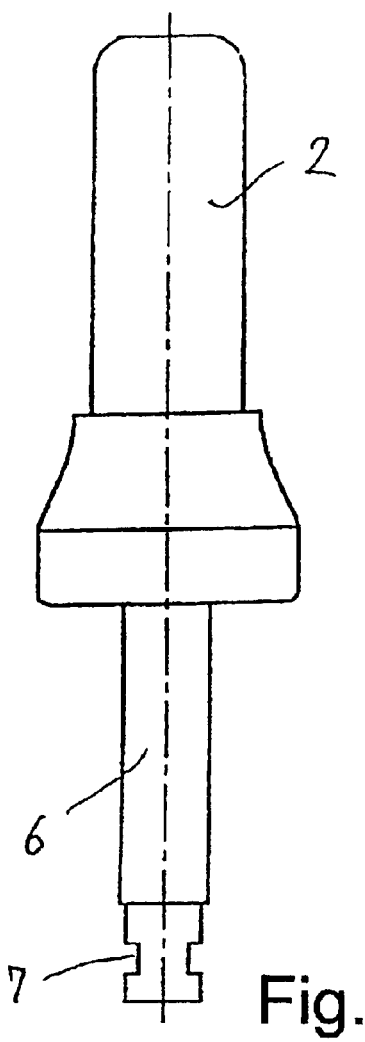
FIG. 5 is a front elevational view of a second dental abrading body embodiment with narrow working surfaces, which are provided with smaller radii.

FIGS. 1 through 4 show a dental abrading body 1, which is provided with oppositely facing abrading or working surfaces 2 and 3 on both sides thereof. Working surface 2 is concave and working surface 3 is convex. The curvature of working surface 3 has a radius R3, which is greater than radius R2 of the curvature of working surface 2.

The working surfaces 2 and 3 are coated with an abrasive material 4, preferably a diamond coating. The dental abrading body 1 is tapered in the area of a front edge 5 to make it easier to introduce the working surfaces 2 and 3 into the interdental spaces 10.

The dental abrading body 1 has a connecting member in the form of a shaft 6 with a locking recess 7 for attachment to a reciprocating drive mechanism 8, schematically shown in the drawing, which is preferably an angular reciprocating drive mechanism. This reciprocating drive mechanism 8 is used to set the dental abrading body 1 into an abrasion movement in the longitudinal direction thereof.

To treat crowding, the dental abrading body 1 is introduced vertically between teeth 9, i.e. in their longitudinal direction. The reciprocating drive mechanism 8 is then used to introduce a linear abrasion movement into the dental abrading body 1 in its longitudinal direction. Due to this abrasion movement, the working surfaces 1 and 2 in the contact area of two teeth 9 form a concave contact surface 11 and a convex contact surface 12, respectively, which engage after completion of treatment. Thus, an interdental contact is produced in the form of an overlapping dimeric dental arch chain of teeth, which is distinguished by excellent pressure stability. This ensures contact and position stability of the adjacent teeth 9. The stability of this arrangement guards against recurrence of misalignments after a correction of misaligned tooth positions and prevents or reduces tertiary crowding.

Figure 6:
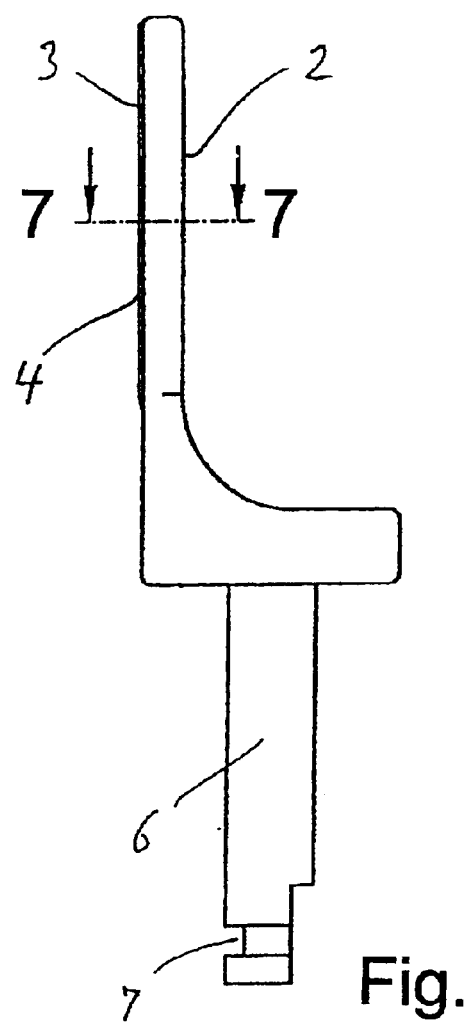
FIG. 6 is a side elevational view of the dental abrading body of FIG. 5.
Figure 7:
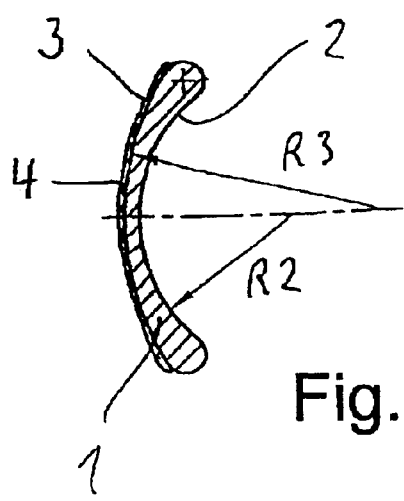
FIG. 7 is a cross-sectional view taken along line 7—7 of FIG. 6.
Figure 8:
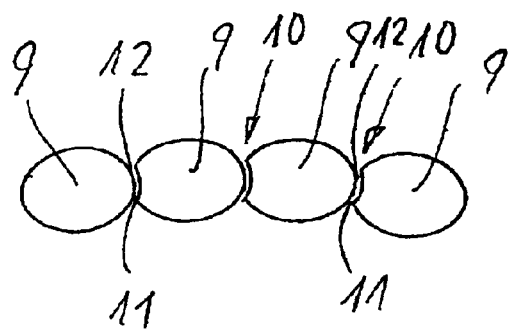
FIG. 8 is a plan view of a stabilized row of teeth.

FIGS. 5 to 7 of the drawings show a dental abrading body 1 with working surfaces 2 and 3 that are reduced in width. Furthermore, working surfaces 2 and 3 have smaller radii R2 and R3 than the illustrative embodiment shown in FIG. 1. In other respects, only the convex working surface 3 is coated with an abrasive material 4. The concave working surface 2 in this case acts merely as a guide surface along the natural convex contact surface 12 of tooth 9, which makes contact during treatment. Consequently, the naturally convex curvature of this contact surface 12 is retained. Only in the opposite tooth in the contact area, a concave contact surface 11 is shaped with radius R3 of the convex working surface 3 of the dental abrading body 1. Here, too, the dental abrading body 1 is linearly driven by means of a reciprocating drive mechanism 8, which is mounted to the locking recess 7 of shaft 6.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method for treating tooth crowding said method comprising:

providing an abrading body having two sides with oppositely lying working surfaces, said abrading body having a connector for attachment to a reciprocating drive mechanism, wherein one working surface has a convex cross-sectional shape having a radius of curvature R3, and the other working surface has a concave cross-sectional shape having a radius of curvature R2, wherein the radius of curvature of the convex working surface is greater than the radius of curvature of the concave working surface and abrading the surface of multiple teeth vertically with said abrading body to produce concave and convex interdental contact surfaces between multiple teeth to produce an overlapping dimeric arcuate chain of teeth wherein said abrading body simultaneously abrades the surface of adjacent teeth to produce concave and convex interdental contact surfaces wherein both working surfaces of said abrading body are coated with an abrasive.

2. The method of claim 1 wherein during the step of abrading, the concave working surface of the abrading body adapts a convex contact surface of a first tooth to the radius of the concave contact surface of an adjacent tooth.

3. The method of claim 1, wherein during the step of abrading, the concave contact surface of an adjacent tooth is adapted to have a radius greater than the radius of the convex contact surface of a first tooth.

* * * * *